May 21, 1946. P. BROWN, JR Plant Pat. 690
BARBERRY PLANT
Filed Aug. 22, 1945
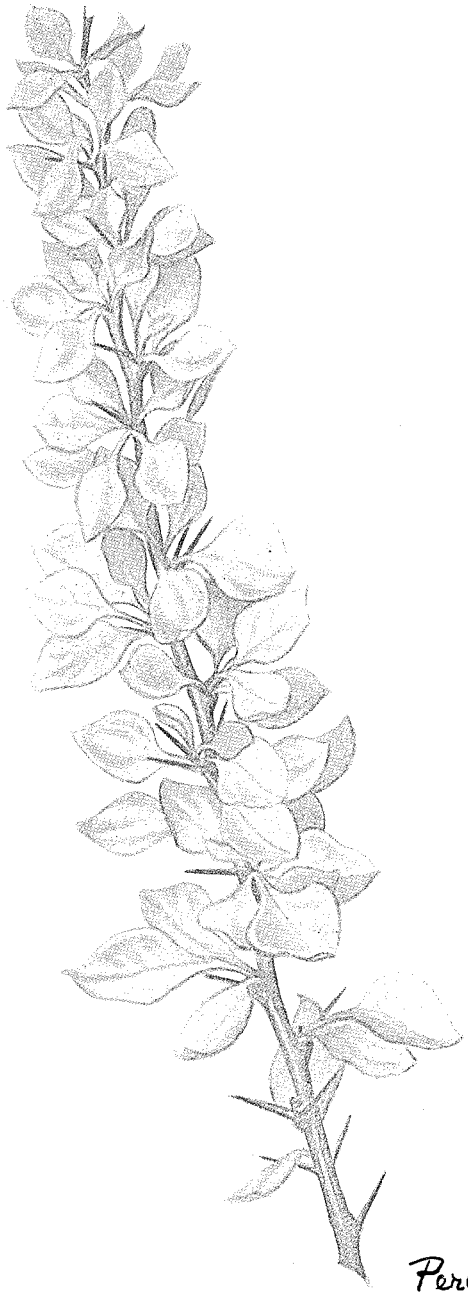
Percy Brown Jr.
By Orville M. Kile
PLANT PATENT AGENT Patented May 21, 1946

Plant Pat. 690

UNITED STATES PATENT OFFICE

690

BARBERRY PLANT

Percy Brown, Jr., Gibraltar, Pa., assignor to Percy Brown Nursery, Gibraltar, Pa.

Application August 22, 1945, Serial No. 612,115

1 Claim. (Cl. 47—59)

My present invention relates to a new and improvide variety of barberry plant which was discovered by me several years ago while planting a large number of *Berberis thunbergi*. Presumably it is a chance seedling produced from this variety. Its golden color attracted my attention and I watched it throughout several seasons. I noted also that the plant was very dwarf and compact in growth.

I then asexually propagated a number of plants from this plant and found the new plants to possess the same characteristics as the original.

The accompanying illustration shows a typical branch of my new variety of barberry plant in July, reproduced in as nearly the true colors as the artist could make them.

Following is a detailed description of my new variety of barberry plant, color plate references being in accord with Ridgway's Color Standards and Nomenclature.

*Description*

Growth habit: Very dwarf, attaining a height of only 18 to 24 inches in more than ten years. The breadth of the plant is about the same as the height and the growth is very compact.

Stems: Old wood, dark brown. New wood, same color as leaves but with brownish streaks. Slender but sturdy and stiff.

Thorns: Thin, sharp thorns about ⅜ inch long are arranged singly at the leaf axils along the length of the stem.

Foliage:

*Color.*—General color effect is bright golden yellow. Ranges from Amber Yellow (Plate VI) to Cosse Green (Plate V), but is principally Picric Yellow (Plate IV), Light Greenish Yellow (Plate V), Greenish Yellow (Plate V), and Green Yellow (Plate V). Leaves at base of stem are Pinard Yellow (Plate IV) to Amber Yellow (Plate VI) and leaves toward the tips of the young growth are marked with a reddish tinge. The under surface of the petals is Straw Yellow (Plate XVI) to light Green-Yellow (Plate V). All colors are much brighter in the Spring at the beginning of the growing season.

*Arrangement.*—Very closely spaced. In groups of three or more.

*Form.*—Leaflets oval with long slender shank.

*Size.*—Rounded portion is ½ to ¾ inch long with the addition of a shank about half this length. Width is about ⅓ to ½ inch.

Flowers: Small flowers are borne singly and in groups of 2 or 3.

Fruit: Small red seed pods are produced but they are not fertile in any respect.

Having thus disclosed my discovery, I claim:

The new and distinct variety of barberry plant of general type of the *Berberis thunbergi* substantially as herein disclosed, characterized particularly by its dwarf growth; the bright golden color of its foliage; and the absence of fertility of its seed pods.

PERCY BROWN, JR.